United States Patent [19]  
Gennari

[11] Patent Number: 4,789,666  
[45] Date of Patent: Dec. 6, 1988

[54] CYTIDINE-DIPHOSPHOCHOLINE SALTS, PARTICULARLY SUITABLE FOR ORAL USE

[75] Inventor: Federico Gennari, Truccazzano, Italy

[73] Assignee: Bioresearch Spa, Liscate, Italy

[21] Appl. No.: 878,697

[22] Filed: Jun. 26, 1986

[30] Foreign Application Priority Data

Jul. 5, 1985 [IT] Italy ................. 21447 A/85

[51] Int. Cl.$^4$ ............ C02H 19/10; A61K 27/00; C07D 51/52
[52] U.S. Cl. .................. 514/51; 536/23; 536/29; 514/44; 514/49; 514/50; 514/52
[58] Field of Search ............ 536/29; 514/51

[56] References Cited

U.S. PATENT DOCUMENTS 3,687,932  8/1972  Nakamachi et al. ............ 536/29

FOREIGN PATENT DOCUMENTS 0184248  6/1986  European Pat. Off. ............ 514/46

| 0075382 | 11/1970 | Japan | 536/29 |
| 0074595 | 9/1973 | Japan | 536/29 |
| 0075999 | 5/1982 | Japan | 536/29 |
| 0108098 | 6/1982 | Japan | 536/29 |
| 0109099 | 6/1982 | Japan | 536/29 |

Primary Examiner—Johnnie R. Brown  
Assistant Examiner—L. Eric Crane  
Attorney, Agent, or Firm—Stevens, Davis, Miller & Mosher

[57] ABSTRACT

New cytidine-diphosphocholine (CDP-choline) salts with long-alkyl chain sulphonic acids suitable for injectable pharmaceutical formulations, but more specifically for oral formulations.

Said salts are prepared by a process comprising preparing an aqueous solution of basic CDP-choline, preparing an aqueous sulphonic acid solution, reacting these two solutions together to obtain the required salt, and recovering this salt with a high degree of purity.

2 Claims, No Drawings

CYTIDINE-DIPHOSPHOCHOLINE SALTS, PARTICULARLY SUITABLE FOR ORAL USE

This invention relates to new cytidine-diphosphocholine (CDP-choline) salts with long-alkyl chain sulphonic acids, of general formula:

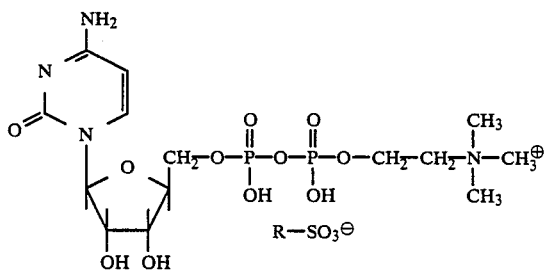

in which R is a linear or branched alkyl radical containing 8 to 18 carbon atoms.

The invention also relates to the process for producing said salts and to the pharmaceutical forms which contain said salts as active principle either alone or together with excipients and auxiliary agents normally used in pharmaceutics.

CDP-choline is the precursor of the biosynthesis of phospholipids. It is widely used in the human clinical field, and is administered in doses of 100–1000 mg per day exclusively by parenteral injection.

In particular, the therapeutic indications of CDP-choline are represented by disturbances of consciousness deriving from cranial traumas or from pathological situations such as cerebral hemorrhages, cerebral thrombroses, arteriosclerotic cerebropathies, Parkinson's disease and Parkinson-like syndromes.

As stated heretofore, the clinical use of CDP-choline is limited to parenteral administration. In this respect, because of its poor absorbability on oral administration, no pharmaceutical preparations are available commercially which allow this method of administration, and this obviously represents a serious limitation to its therapeutic use, particularly in prolonged treatment cycles.

This drawback is obviated by the CDP-choline salts according to the present invention, which show a bioavailability on oral administration which is considerably higher than that of basic CDP-choline or its sodium salt normally used in therapy, thus enabling it to be also used in oral formulations.

The process for preparing cytidine-diphosphocholine (CDP-choline) salts with long-alkyl chain sulphonic acids according to the present invention is characterised by preparing an aqueous solution of basic CDP-choline, preparing an aqueous sulphonic acid solution, reacting the two solutions together to obtain the required salt, and recovering this salt with a high level of purity.

These and further characteristics of the process according to the present invention, and of the products obtained and the relative pharmaceutical formulations, will be more apparent from the detailed description given hereinafter of preferred embodiments of the invention and of administration trials.

The aqueous solution of basic CDP-choline is prepared by dissolving commercial CDP-choline sodium salt in distilled water in a concentration of between 5% and 20% w/v, and eliminating the sodium ion by passage through a column containing a strongly acidic cation exchanger in H+ form in a quantity of between 1 and 10 liters of resin per mole of CDP-choline, and preferably 2 liters per mole of CDP-choline.

The resins preferably used are:

| Amberlite | IR 120 |
| Dowex | 50 W-X 8 |
| Duolite | C 20 |

By this treatment a solution of basic CDP-choline can be obtained in a concentration variable between 3% and 20%, and preferably 15%, w/v.

The aqueous sulphonic acid solution is preferably prepared by dissolving the sodium salt of the required sulphonic acid in distilled water at a temperature of between 20° C. and 80° C. according to its solubility in water, to a concentration of between 5% and 30% w/v, and eliminating the sodium ion by passage through a column containing a strongly acidic cation exchanger in H+ form, in a quantity of between 1 and 10 liters of resin per mole of sulphonic acid, and preferably 2 liters of resin per mole of sulphonic acid.

The resins preferably used are:

| Amberlite | IR 120 |
| Dowex | 50 W-X 8 |
| Duolite | C 20 |

By this treatment a solution of the required sulphonic acid can be obtained in a concentration varying between 3% and 25% w/v, and preferably 20% w/v.

The sulphonic acid sodium salts of formula $R\text{-}SO_3Na$ in which R is a linear or branched alkyl chain of 6 to 18 carbon atoms are easily prepared by reacting the corresponding bromides with sodium sulphite in accordance with the equation:

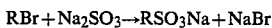

in which R is as heretofore defined.

The procedure for this preparation is as already described in patent application No. 20940 A/84 (Italy) of the present applicant.

To obtain the salts according to the invention, the reaction is carried out by mixing together, under agitation at ambient temperature for a time of between 10 and 30 minutes, the two solutions prepared as heretofore described in such volumes that the basic CDP-choline and the sulphonic acid are in equimolar quantities.

The salts (CDP-choline sulphonates) are recovered from the resultant solution by lyophilisation or by drying in a spray-dryer.

As heretofore stated, the CDP-choline salts according to the present invention display a considerably greater bioavailability than the commercial sodium salt when administered orally, as can be seen from the results of the following trial which was carried out on male rats of weight 174–218 g, under fasting from the previous evening.

The animals were operated on under ether anesthesia, and the products were administered into the duodenum about 6 cm from the pylorus.

The products were administered in 30% propylene glycol in water (v/v) at a dose of 1 g/kg, and corresponded to the following symbols:

| BR 1280 | CDP-choline sodium salt |

-continued

| | |
|---|---|
| BR 742 | CDP-choline octanesulphonate |
| BR 743 | CDP-choline decanesulphonate |
| BR 744 | CDP-choline dodecanesulphonate |
| BR 745 | CDP-choline tetradecanesulphonate |
| BR 746 | CDP-choline hexadecanesulphonate |
| BR 747 | CDP-choline octadecanesulphonate |

The basal samples were obtained by treating the animals with 30% propylene glycol in water (v/v).

The volume injected was 5 ml/kg. The values obtained represent the mean of the values of five animals per product.

The animals were sacrificed under ether anesthesia, and blood samples were withdrawn from the portal vein and from the abdominal aorta, 10 minutes after administration.

The blood samples were deproteinised in 0.8M $HClO_4$ (1:1) and centrifuged in SORVALL for 15 minutes a 12,000 r.p.m.

After adjusting to about pH 4, 200 μl portions of deproteinised blood were injected for HPLC analysis. The standards were prepared by adding BR 1280 concentrations corresponding to 20-50-100 μg/ml to 1 ml portions of blood.

| Chromatographic conditions: | |
|---|---|
| Eluent: | 0.2 M ammonium formate, pH 4 |
| Throughput: | 1 ml/min. Loop = 200 μl |
| Column: | PARTISIL 10 SCX Whatman |
| Detector: | UV = 280 nm, AUFS = 0.4 |

A calculation was made by comparison with blood samples of known Br 1280 content prepared by adding the substance to the biological liquid.

Table 1 shows the concentrations of CDP-choline in the portal and aortic blood 10 minutes after intraduodenal administration of 1 g/kg of CDP-choline sodium salt and of the new CDP-choline salts according to the invention.

TABLE 1

| Product | portal blood (μg/ml) | aortic blood (μg/ml) |
|---|---|---|
| BR 1280 | 3.6 | 0.055 |
| BR 742 | 107 | 1.6 |
| BR 743 | 161 | 2.8 |
| BR 744 | 203 | 4.2 |
| BR 745 | 215 | 4.8 |
| BR 746 | 201 | 4.1 |
| BR 747 | 162 | 2.8 |

(the values are expressed as basic CDP-choline)

As can be seen from these data, considerably higher hematic concentrations are obtained, particularly in the portal blood, after intraduodenal administration of the new CDP-choline salts than in the case of CDP-choline sodium salt.

A second trial was carried out for the products BR 1280, BR 743, BR 744, BR 745, BR 746, BR 747 by administering 200 mg/kg of product and evaluating only the concentration in the portal blood after 10 minutes.

The data are given in Table 2.

TABLE 2

| Product | Portal blood (g/ml) |
|---|---|
| BR 1280 | 0.6 |
| BR 743 | 29.5 |
| BR 744 | 36.3 |
| BR 745 | 40 |
| BR 746 | 35.2 |
| BR 747 | 27.1 |

The hematic concentrations are again considerably greater for the salts according to the invention. These salts can be presented in injectable formulations, but more specifically in oral formulations such as tablets, pills, sustained-release capsules, sustained-release tablets, gastroresistant tablets, sachets, syrups, extemporaneous syrups, sustained-release syrups and other forms normally used in pharmaceutics.

The examples given hereinafter illustrate the method for preparing the new CDP-choline salts, these examples being given to illustrate the invention, but without limiting it.

EXAMPLE 1

Preparation of CDP-choline octanesulphonate

A column is prepared containing 20 liters of Amberlite IR 120 resin in H+ form, carefully activated with 6N HCl and then washed with distilled water until the eluate is neutral.

Separately, 5.10 kg of commercial CDP-choline sodium salt are dissolved in 25 liters of distilled water and the solution is passed through the previously prepared column. This is washed with water until the CDP-choline disappears from the eluate. The CDP-choline solution is concentrated under vacuum to a volume of 35 liters.

In this manner 35 liters of solution containing 4.9 kg of basic CDP-choline are obtained. Separately, a second column of Amberlite IR 120 resin in H+ form is prepared, is carefully activated with 6N HCl and then washed with distilled water until the eluate is neutral.

2.165 kg of sodium octanesulphonate are dissolved in 50 liters of distilled water at 40° C., and the solution thus obtained is passed through the previously prepared column.

This is washed with 20 liters of distilled water to obtain 70 liters of a solution containing 1.945 kg of octanesulphonic acid.

This solution is concentrated to 50 liters by boiling, and cooled to 20° C.

The basic CDP-choline solution is mixed with the octanesulphonic acid solution at ambient temperature under agitation for 20 minutes. The homogeneous solution obtained is lyophilised. In this manner, 7 kg of a white powder are obtained, showing the following composition on analysis:

| | |
|---|---|
| CDP-choline | 69.7% |
| Octanesulphonic acid | 27.8% |
| $H_2O$ | 2.5% |

The product is in the form of a white powder soluble in water, methanol, ethanol and 2:1 methanol-chloroform mixtures.

On HPLC analysis (column PARTISIL 10 SCX, eluent 0.1M ammonium formate, throughput 1 ml/min) the product shows a single peak with a retention time of 550 seconds, exactly corresponding to that of commercial CDP-choline sodium salt.

| Elementary analysis: $C_{14}H_{26}N_4O_{11}P_2 \cdot C_8H_{18}O_3S \cdot H_2O$ | | | |
|---|---|---|---|
| | N | C | H |
| Calculated % | 8.00 | 37.69 | 6.62 |
| Found % | 7.95 | 37.58 | 6.67 |

The product ultraviolet spectrum (in 0.1N HCl) shows an absorption maximum at 280 nm with $E_{1\%}=183.4$.

EXAMPLE 2

Preparation of CDP-choline decanesulphonate

The procedure of Example 1 is followed but using 2.445 kg of sodium decanesulphonate dissolved in 60 liters of distilled water at 40° C.

7.3 kg of a white powder are obtained, showing the following composition on analysis:

| CDP-choline | 67.0% |
|---|---|
| Decanesulphonic acid | 30.5% |
| $H_2O$ | 2.5% |

The product is in the form of a white powder soluble in water, methanol, ethanol and 2:1 methanol-chloroform mixtures.

On HPLC analysis (column PARTISIL 10 SCX, eluent 0.1M ammonium formate, throughput 1 ml/min) the product shows a single peak with a retention time of 550 seconds, exactly corresponding to that of commercial CDP-choline sodium salt.

| Elementary analysis: $C_{14}H_{26}N_4O_{11}P_2 \cdot C_{10}H_{22}O_3S \cdot H_2O$ | | | |
|---|---|---|---|
| | N | C | H |
| Calculated % | 7.69 | 39.54 | 6.92 |
| Found % | 7.81 | 39.47 | 6.94 |

The product ultraviolet spectrum (in 0.1N HCl) shows an absorption maximum at 280 nm with $E_{1\%}=176.2$.

EXAMPLE 3

Preparation of CDP-choline dodecanesulphonate

The procedure of Example 1 is followed but using 2.725 kg of sodium dodecanesulphonate dissolved in 60 liters of distilled water at 40° C.

7.6 kg of a white powder are obtained, showing the following composition on analysis:

| CDP-choline | 64.5% |
|---|---|
| Dodecanesulphonic acid | 33.1% |
| $H_2O$ | 2.4% |

The product is in the form of a white powder soluble in water, methanol, ethanol and 2:1 methanol-chloroform mixtures.

On HPLC analysis (column PARTISIL 10 SCX, eluent 0.1M ammonium formate, throughput 1 ml/min) the product shows a single peak with a retention time of 550 seconds, exactly corresponding to that of commercial CDP-choline sodium salt.

| Elementary analysis: $C_{14}H_{26}N_4O_{11}P_2 \cdot C_{12}H_{26}O_3S \cdot H_2O$ | | | |
|---|---|---|---|
| | N | C | H |
| Calculated % | 7.40 | 41.25 | 7.19 |
| Found % | 7.43 | 40.95 | 7.25 |

The product ultraviolet spectrum (in 0.1N HCl) shows an absorption maximum at 280 nm with $E_{1\%}=169$.

EXAMPLE 4

Preparation of CDP-choline tetradecanesulphonate

The procedure of Example 1 is followed, but using 3 kg of sodium tetradecanesulphonate dissolved in 120 liters of distilled water at 50° C., the column being controlled at this temperature.

Instead of being lyophilised, the final solution is dried in a spray-dryer, operating with inlet air at 160° C. and continuously extracting the dry product.

7.8 kg of a white powder are obtained, showing the following composition on analysis:

| CDP-choline | 62.2% |
|---|---|
| Tetradecanesulphonic acid | 35.5% |
| $H_2O$ | 2.3% |

The product is in the form of a white powder soluble in water, methanol, ethanol and 2:1 methanol-chloroform mixtures.

On HPLC analysis (column PARTISIL 10 SCX, eluent 0.1M ammonium formate, throughput 1 ml/min) the product shows a single peak with a retention time of 550 seconds, exactly corresponding to that of commercial CDP-choline sodium salt.

| Elementary analysis: $C_{14}H_{26}N_4O_{11}P_2 \cdot C_{14}H_{30}O_3S \cdot H_2O$ | | | |
|---|---|---|---|
| | N | C | H |
| Calculated % | 7.14 | 42.83 | 7.46 |
| Found % | 7.23 | 42.92 | 7.41 |

The product spectrum (in 0.1N HCl) shows an absorption maximum at 280 nm with $E_1\%=163.3$.

EXAMPLE 5

Preparation of CDP-choline hexadecanesulphonate

The procedure of Example 1 is followed, but using 3.285 kg of sodium hexadecanesulphonate dissolved in 150 liters of distilled water at 65° C., the column being controlled at this temperature.

8.1 kg of a white powder are obtained, showing the following composition on analysis:

| CDP-choline | 60.1% |
|---|---|
| Hexadecanesulphonic acid | 37.7% |
| $H_2O$ | 2.2% |

The product is in the form of a white powder soluble in water, methanol, ethanol and 1:1 methanol-chloroform mixtures.

On HPLC analysis (column PARTISIL 10 SCX, eluent 0.1M ammonium formate, throughput 1 ml/min) the product shows a single peak with a retention time of 550 seconds, exactly corresponding to that of commercial CDP-choline sodium salt.

| Elementary analysis: $C_{14}H_{26}N_4O_{11}P_2 \cdot C_{16}H_{34}O_3S \cdot H_2O$ | | | |
|---|---|---|---|
| | N | C | H |
| Calculated % | 6.89 | 44.33 | 7.69 |
| Found % | 6.78 | 44.38 | 7.61 |

The product ultraviolet spectrum (in 0.1N HCl) shows an absorption maximum at 280 nm with $E_{1\%} = 157.4$.

EXAMPLE 6

Preparation of CDP-choline octadecanesulphonate

The procedure of Example 1 is followed, but using 3.565 kg of sodium octadecanesulphonate dissolved in 175 liters of distilled water at 80° C., the column being controlled at this temperature.

8.4 kg of a white powder are obtained, showing the following composition on analysis:

| CDP-choline | 58.1% |
|---|---|
| Octadecanesulphonic acid | 39.8% |
| $H_2O$ | 2.1% |

The product is in the form of a white powder relatively poorly soluble in water, but very soluble in methanol, ethanol and 1:1 methanol-chloroform mixtures.

On HPLC analysis (column PARTISIL 10 SCX, eluent 0.1M ammonium formate, throughput 1 ml/min) the product shows a single peak with a retention time of 550 seconds, exactly corresponding to that of commercial CDP-choline sodium salt.

| Elementary analysis: $C_{14}H_{26}N_4O_{11}P_2 \cdot C_{18}H_{38}O_3S \cdot H_2O$ | | | |
|---|---|---|---|
| | N | C | H |
| Calculated % | 6.66 | 45.71 | 7.91 |
| Found % | 6.58 | 45.83 | 7.87 |

The product ultraviolet spectrum (in 0.1N HCl) shows an absorption maximum at 280 nm with $E_{1\%} = 152.1$

EXAMPLE 7

| Preparation of gastroresistant tablets | |
|---|---|
| (a) A 200 mg tablet contains: | |
| CDP-choline tetradecanesulphonate | 322 mg |
| equivalent to CDP-choline | 200 mg |
| Cross-linked sodium carboxymethylcellulose | 70 mg |
| Triethanolamine (neutraliser) | 65 mg |
| Microcrystalline cellulose to make up to | 600 mg |
| Cellulose acetophthalate | 20 mg |
| Diethylphthalate | 6.4 mg |
| Silicone resin | 3.6 mg |
| (b) A 400 mg tablet contains: | |
| CDP-choline hexadecanesulphonate | 666 mg |
| equivalent to CDP-choline | 400 mg |
| Cross-linked polyvinylpyrrolidone | 200 mg |
| Sodium chloride | 200 mg |
| Diethanolamine (neutraliser) | 90 mg |
| Microcrystalline cellulose to make up to | 1300 mg |
| Cellulose acetophthalate | 40 mg |
| Diethylphthalate | 12.8 mg |
| Silicone resin | 7.2 mg |
| (c) A 200 mg tablet contains: | |
| CDP-choline dodecanesulphonate | 310 mg |
| equivalent to CDP-choline | 200 mg |

| -continued | |
|---|---|
| Preparation of gastroresistant tablets | |
| Sodium bicarbonate | 150 mg |
| Citric acid | 75 mg |
| Monoethanolamine (neutraliser) | 28 mg |
| Cellulose acetophthalate | 20 mg |
| Diethylphthalate | 6.4 mg |
| Silicone resin | 3.6 mg |

EXAMPLE 8

| Preparation of capsules | |
|---|---|
| (a) A 200 mg capsule contains: | |
| CDP-choline hexadecanesulphonate | 333 mg |
| equivalent to CDP-choline | 200 mg |
| Triethanolamine (neutraliser) | 65 mg |
| Lactose | 200 mg |
| Magnesium stearate | 12 mg |
| (b) A 200 mg capsule contains: | |
| CDP-choline octadecanesulphonate | 345 mg |
| equivalent to CDP-choline | 200 mg |
| Mannitol | 100 mg |
| Triethanolamine (neutraliser) | 65 mg |
| Lactose | 100 mg |
| Magnesium stearate | 12 mg |

EXAMPLE 9

| Preparation of capsules with sugar-coated pellets | |
|---|---|
| (a) A 200 mg capsule with sugar-coated pellets contains: | |
| CDP-choline tetradecanesulphonate | 322 mg |
| equivalent to CDP-choline | 200 mg |
| Triethanolamine (neutraliser) | 65 mg |
| Sugar-coated pellets | 200 mg |
| (b) A 200 mg capsule with sugar-coated pellets contains: | |
| CDP-choline octaadecanesulphonate | 345 mg |
| equivalent to CDP-choline | 200 mg |
| Triethanolamine (neutraliser) | 65 mg |
| Sugar-coated pellets | 200 mg |

I claim:

1. Cytidine-diphosphocholine (CDP-choline) salts with long-alkyl chain sulphonic acids, of the formula:

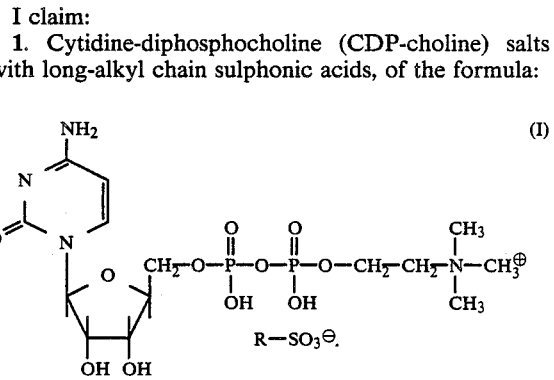

in which R is a linear or branched alkyl radical containing 8 to 18 carbon atoms.

2. Pharmaceutical compositions particularly suitable for oral administration in the treatment of disturbances of consciousness deriving from cranial traumas or from pathological situations including cerebral hemorrhages, cerebral thromboses, arteriosclerotic cerebropathies, Parkinson's disease and Parkinson-like syndromes, comprising at least one compound of general formula (I) as defined in claim 1 as active principle, and a pharmaceutically acceptable carrier.

* * * * *